(12) United States Patent
Harding

(10) Patent No.: US 6,488,501 B1
(45) Date of Patent: Dec. 3, 2002

(54) TRANSFER JIG FOR DENTAL IMPLANTS AND METHOD FOR MAKING A MODEL

(75) Inventor: Stewart Peter Harding, Guernsey (GB)

(73) Assignee: Osteo-Ti Ltd, St Sampsons (GB)

( * ) Notice: Subject to any disclaimer, the term of this patent is extended or adjusted under 35 U.S.C. 154(b) by 0 days.

(21) Appl. No.: 09/701,712

(22) PCT Filed: Jun. 1, 1999

(86) PCT No.: PCT/GB99/01734

§ 371 (c)(1),
(2), (4) Date: Dec. 1, 2000

(87) PCT Pub. No.: WO99/62421

PCT Pub. Date: Dec. 9, 1999

(30) Foreign Application Priority Data

Jun. 2, 1998 (GB) ................................................ 9811869

(51) Int. Cl.⁷ ................................................. A61C 8/00
(52) U.S. Cl. ........................................ 433/173; 433/214
(58) Field of Search ................................ 433/172, 173, 433/214, 215, 174

(56) References Cited

U.S. PATENT DOCUMENTS

| | | | |
|---|---|---|---|
| 4,708,654 A | 11/1987 | Branemark | 433/213 |
| 5,055,047 A | 10/1991 | Names | 433/214 |
| 5,334,024 A | 8/1994 | Niznick | 433/173 |
| 5,904,483 A | * 5/1999 | Wade | 433/214 |
| 5,964,591 A | * 10/1999 | Beaty et al. | 433/173 |
| 6,068,478 A | * 5/2000 | Grande et al. | 433/173 |

FOREIGN PATENT DOCUMENTS

| | | |
|---|---|---|
| DE | 31 10 694 A1 | 9/1982 |
| EP | 0 473 262 A1 | 3/1992 |
| FR | 1.463.860 | 7/1965 |
| WO | 88/03007 | 5/1988 |
| WO | 93/20774 | 10/1993 |
| WO | 96/29019 | 9/1996 |
| WO | 97/28755 | 8/1997 |

* cited by examiner

Primary Examiner—Cary E. O'Connor
(74) Attorney, Agent, or Firm—Nixon & Vanderhye P.C.

(57) ABSTRACT

A transfer jig for implant dental surgery uses a tubular post and a tubular coping which is attachable and detachable from the post by a snap-fit attachment. The post has a hexagonal portion for location in a hexagonal socket in an implant and a frusto-conical portion which is a seat for the coping. The coping has a diametrically opposed pair of slots in its end that seats on the post to receive a diametrically opposed pair of pins with a snap-fit, the pins being mounted on the post so that the coping is precisely located relative to the hexagonal portions. The coping also has apertures formed through its tubular wall through which dental impression material is forced to form structural links when a dental impression is taken.

22 Claims, 7 Drawing Sheets

TRANSFER JIG FOR DENTAL IMPLANTS AND METHOD FOR MAKING A MODEL

This invention relates to a method for making a model for a dental prosthesis for mounting in a dental foundation member such as an implant having an internal hex, the implant being embedded in a jawbone of a patient, and a dental formation mounting arrangement for use in such a method.

After a period of, for example, three to six months, has been allowed for an implant in the jawbone of a patient to settle, it is usual for an impression to be made in a plastic material of the surfaces of at least part of the gum, and any adjacent teeth that surround the embedded implant. The impression is then used to make a model of that part of the gum and the adjacent teeth. A dental technician uses the model to make a dental prosthesis, which may be in the form of a false tooth, for fitting into a socket in the implant.

An integrated implant prosthesis must fit accurately and be designed to optimise stress distribution to the supporting bone. It is therefore essential for this prosthetic restoration of an implant that the position of each implant in a jaw bone be accurately recorded and transferred to the model. This is particularly important for a screw retained prosthesis.

In practice, relative orientation of the implant to the desired orientation of the dental prosthesis it is to support is unpredictable, both because the actual location of the settled implant is difficult to predict and because the dental surgeon may have to overcome one or more of a number of problems when implanting the implant which means that the orientation of the implant may differ from the optimum.

WO93/20774 discloses a dental formation mounting arrangement comprising a locating element which is adapted to be engaged in a socket formed in a dental foundation member on which the dental formation is to be mounted so as to be held against rotation relative to the dental foundation member and fixing means for fixing the locating element to the foundation member when the locating element is so engaged in the socket, wherein the dental formation mounting arrangement comprises a locating bush which is to be fitted over the locating element, when the latter is engaged in the socket and which is to carry said dental formation.

WO93/20774 further discloses a method of making a model of at least part of the gum utilising the dental formation mounting arrangement described above. The arrangement is described as comprising essentially three components and, due to the configuration of the components, requires the use of a non-standard impression tray which is specific to the mounting arrangement.

WO96/29019 discloses a dental formation mounting arrangement including an anchor pin or post with an elastic clamp head which is screwed into a tapped hole in an implant which is implanted in the jawbone of a patient, and a contoured element which is snap-fitted onto the anchor pin. The contoured element may be an impression cap or tray, a crown cap or a secondary pin or post. The snap-fitting comprises an annular shoulder which is formed internally on the contoured element and which engages the elastic clamp head in a snap-fit manner. The relative orientation of the contoured element to the implement is imprecise because the anchor pin or post is screwed into the implant and the contoured element can be fitted onto it at random.

According to one aspect of this invention there is provided a dental formation mounting arrangement including a locating element having a portion which is formed so as to be a snug fit in a socket formed in a dental foundation member on which a dental formation is to be mounted, fixing means for fixing the locating element to the foundation member when the locating element portion is fitted into the socket, and a mating element attachable to and detachable from the locating element by means which provide a snap-fit attachment, wherein said locating element has a flat surface which is adapted to make face to face contact with a corresponding flat surface of the socket when that locating element portion is fitted into the socket whereby to hold the locating element against rotation relative to the dental foundation member and each of the locating and mating elements is provided with a respective formation, the formations on the locating and mating elements being adapted to be positively interengaged when the mating element is snap-fitted onto the locating element and the mating element is in a certain orientation relative to said flat surface.

Preferably the mating element is a hollow body provided with apertures in its structure which place its interior in communication with its surrounds, the arrangement being such that, when the mating element is embedded in dental impression material during a process of making a dental impression, such dental impression material can extend through the apertures and form structural links between such dental impression material within the interior of the hollow body and such dental impression material that surrounds the hollow body. The means for providing a snap-fit may comprise at least one locating member which protrudes from one of the locating and mating elements, the at least one locating member being locatable in a corresponding recess formed in the other of the locating and mating elements, the at least one locating member and the corresponding recess serving as the formations. The at least one locating member may comprise one or more locating pins and may protrude from the locating element and be locatable in a respective slot in the mating element.

In another embodiment the locating and mating elements are adapted to be snap-fitted together by pushing a projecting portion of one of them into a cavity formed in the other and the formations include a wall which extends partway around the mouth of the cavity and which seats substantially without clearance in a corresponding recess formed in the one of the locating and mating elements, movement of the other element relative to the one element in the direction that would displace the wall around the periphery of the cavity being stopped by abutment with the ends of the recess in which the wall seats without substantial clearance.

Conveniently the locating element is formed from metal and the mating element is formed from a plastics material. The mating element may include at least one flange which is embedable in a dental impression material in use, enabling the mating element to be removed with the impression material once the impression material has set.

According to another aspect of this invention there is provided a method for making a model of at least part of the gum and one or more adjacent teeth that surround one or more dental foundation members embedded in the jawbone of a patient, said one or more dental foundation members each having a receiving socket therein, the method including the steps of:
  (i) locating a locating element in the socket of the or each dental foundation member;
  (ii) attaching a mating element to the locating element by means of a snap-fit;
  (iii) placing a dental impression tray filled with dental impression material around the teeth, gums and the or each dental foundation member;
  (iv) removing the impression tray and dental impression material with the mating element embedded therein from the mouth of the patient by overcoming the snap-fit holding the mating element on the locating element once the dental impression material has set; and (vii) forming a replica of the teeth and gums of the patient using the impression created in the dental impression material once set, as a maul; wherein the method also includes (viii) providing the socket and a portion of the locating element which is located in the socket with mating flat faces which make face to face contact with one another when the locating element is located in the socket whereby the locating element is held against rotation relative to the dental foundation member; and (ix) positively interengaging certain formations provided on the locating and mating elements so that the mating element is in a certain orientation relative to said dental formation member.

Preferably the method includes the step of selecting a hollow body as the mating element, the hollow body having apertures in its structure which place its interior in communication with its surrounds and, filling the interior with dental impression material so that it extends through the apertures and forms structural links between the dental impression material within the hollow body and the dental impression material that surrounds the body in the tray.

Three forms of transfer jig and a method for forming a dental prosthesis for mounting in a dental foundation member, such as an implant, which embodies this invention are described now by way of example with reference to the accompanying drawings, of which.

After an implant has been implanted into the jawbone of a patient, it is typical to allow the implant to settle in the bone and to allow the bone to grow around the implant over a period of, for example, three to six months. Subsequently, but prior to making an impression of the gum in which one or more implants have been implanted, a dental surgeon fits a transfer jig into a standard hexagonal socket of the or each implant by removing the soft gum tissue that had grown over it since it was implanted.

Figure 1:
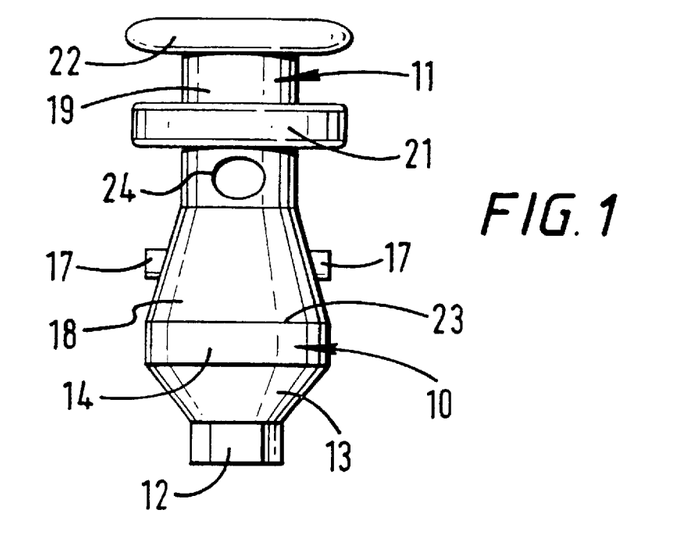
FIG. 1 is a side elevation of one form of transfer jig.
Figure 2:
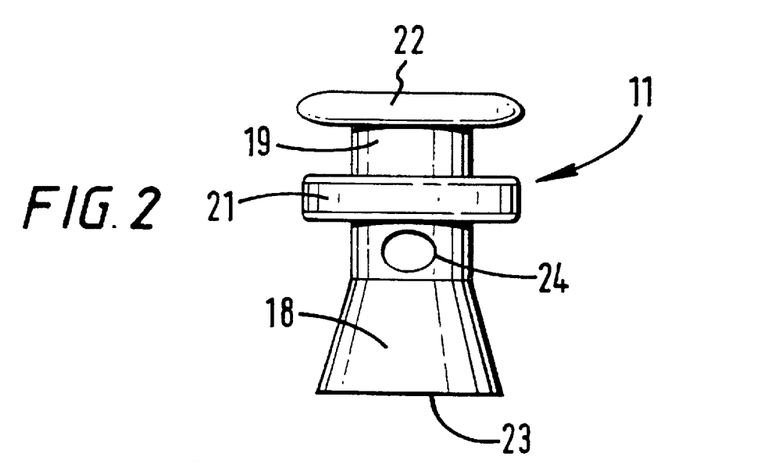
FIG. 2 is a side elevation of the coping of the transfer jig shown in FIG. 1.
Figure 3:
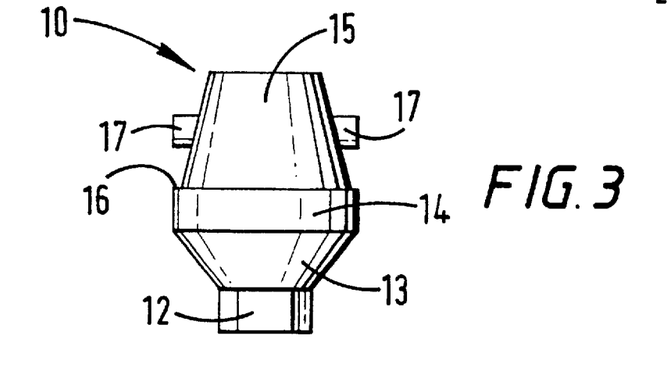
FIG. 3 is a side elevation of the post of the transfer jig shown in FIG. 1.

FIGS. 1 to 3 show the elements of such a transfer jig are a first locating element 10, which is known as a post, and a second mating element 11, which is known as a coping and which is attachable and detachable from the post 10 by means of a snap fit. Both the post 10 and the coping 11 are generally tubular. The post 10, which is conveniently formed of a metal such as titanium, has a hexagonal portion 12 at one end for location in a mating hexagonal socket of an implant (not shown). The hexagonal portion 12 may be provided with one flat surface (not shown) which is adapted to abut a corresponding flat surface formed in the socket of the implant to hold the post 10 against rotation relative to the implant.

The hexagonal portion 12 projects coaxially from the smaller diameter end of one frusto-conical portion 13 of the post 10. A cylindrical portion 14 extends coaxially from the larger diameter end of the frusto-conical portion 13 and is located between that frusto-conical portion 13 and another coaxial frusto-conical portion 15. The other frusto-conical portion 15 tapers away from the cylindrical portion 14 and the diameter of its larger diameter end is less than the diameter of the cylindrical portion 14 so that an annular shoulder 16 is formed around it.

Two locating pins 17, which are integral with the remainder of the post 10, project from the outer surface of the other frusto-conical portion 15 and are located substantially diametrically opposite one another.

A fixing screw (not shown) is insertable through the bore of the generally tubular post 10, the threaded free end of the screw being engageable with a threaded portion in the socket of the implant (not shown) to which the post 10 is to be attached, to secure the post 10 in place with the hexagonal portion 12 located in the hexagonal socket of the implant.

The coping 11, which is preferably made of plastics material, has a hollow frusto-conical portion 18 at one end. A cylindrical portion 19 extends coaxially from the smaller diameter end of the frusto-conical portion 18 and has an axially-spaced pair of radially-outwardly extending annular flanges 21 and 22. The flange 21 is intermediate the ends of the cylindrical portion 19. The flange 22 is at the end of the cylindrical portion 19 that is remote from the frusto-conical portion 18.

The interior of the frusto-conical portion 18 of the coping 11 is shaped to receive the frusto-conical portion 15 of the post 10 so as to seat thereon.

Two opposing slots (not shown) are formed in the walls of the frusto-conical portion 18 of the coping 11, each being for receiving a respective one of the locating pins 17 in a snap-fit manner. In a preferred embodiment each slot is substantially keyhole-shaped having one portion which extends from the rim 23 at the larger diameter end of the frusto-conical portion 18 and which is tapered and another portion which is an aperture and which is at the smaller end of the tapered portion, the width of the aperture being greater than the width of the tapered portion at its smaller diameter end and being sized so that a locating pin 17 fits snugly therein with opposite sides of the slot in contact with opposite sides of the locating pin 17 snap-fitted therein.

One or more apertures 24 extend through the walls of the cylindrical portion 19 of the coping 11 between the frusto-conical portion 18 and the nearer flange 21.

FIGS. 4 to 7 show an alternative form of generally tubular coping 11A for use with the post 10. Parts of the coping 11A which are similar to corresponding parts of the coping 11 described above are identified by the same reference number with A added.

Figure 4:
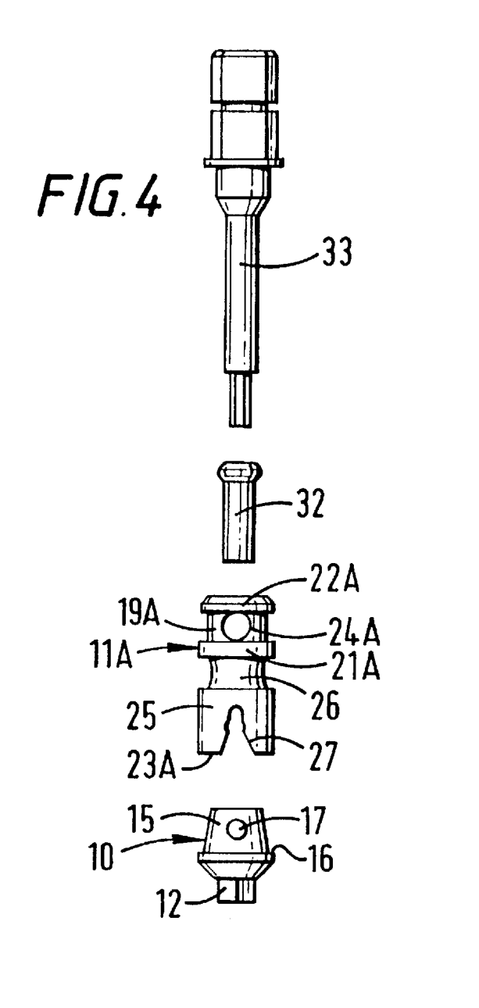
FIG. 4 is a parts exploded side elevation of an alternative transfer jig which includes the post of FIG. 3 and an alternative form of coping.
Figure 5:
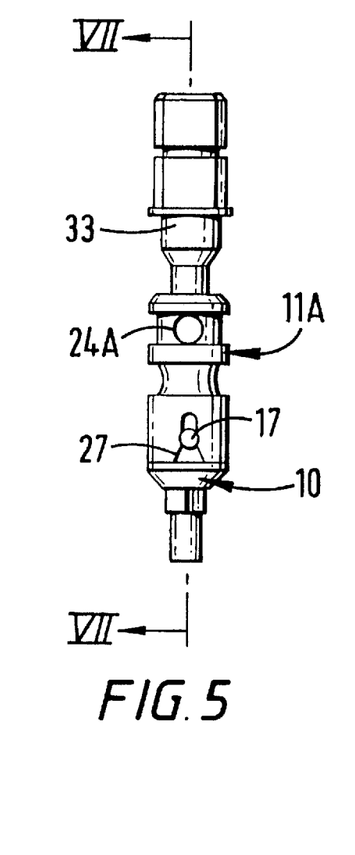
FIG. 5 is a side elevation of the transfer jig of FIG. 4 in the assembled condition.

Instead of the hollow frusto-conical portion 18 at one end of the cylindrical portion 19A of the coping 11A, the coping 11A has a hollow cylindrical portion 25 which has an outside diameter which is greater than that of the cylindrical portion 19A. The exterior of the cylindrical portion 19A between the intermediate flange 21A and the larger diameter cylindrical portion 25 forms a concave annular surface 26. Like the hollow frusto-conical portion 18, the interior of the hollow cylindrical portion 25 is shaped to receive the frusto-conical portion 15 of the post 10 so as to seat thereon. Two slots 27 are formed in the sidewall of the hollow cylindrical portion 25 to receive the locating pins 17. The slots 27 are diametrically opposite one another and each opens into the rim 23A of the cylindrical portion 25. The profile of each of the slots 27 is such as to define a U-shaped base portion which extends into a bulbous portion, the bulbous portion being at the smaller end of a tapering portion, which tapers inwardly from the rim 23A of the hollow cylindrical portion 25, and being sized to snugly receive a locating pin 17 as shown in FIG. 5.

Figure 6:
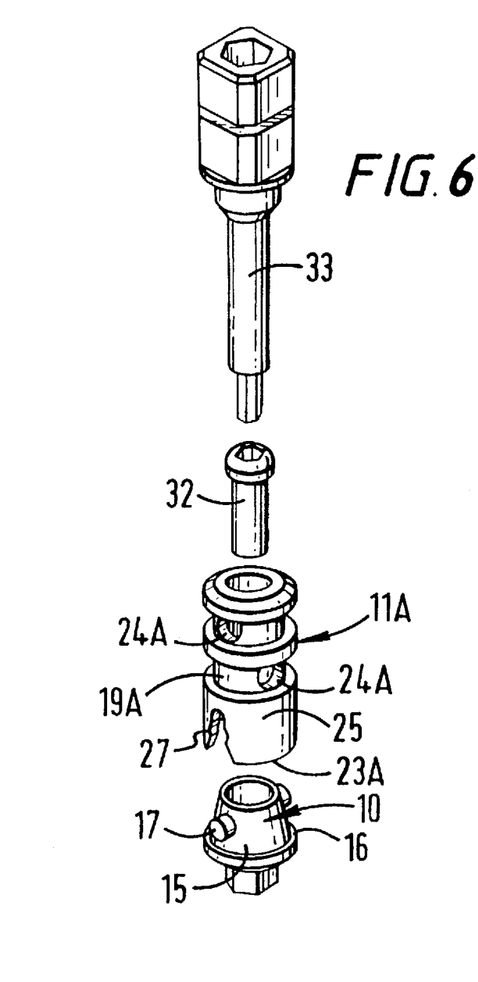
FIG. 6 is a parts exploded perspective view of the transfer jig of FIG. 4.

FIG. 6 shows apertures 24A formed in the cylindrical portion 19A on either side of the annular flange 21A and angularly offset one with respect to another about the axis of the generally tubular coping 11A. Each aperture 24A extends through the tubular wall of the cylindrical portion 19A, communicating at its inner end with the bore 28 (see FIG. 7) of the coping 11A and being open at its other end in the outer surface of the cylindrical portion 19A. The diameter of each aperture 24A is substantially equal to the distance between the flange 21A and the flange 22A or the hollow cylindrical portion 25 respectively.

Figure 7:
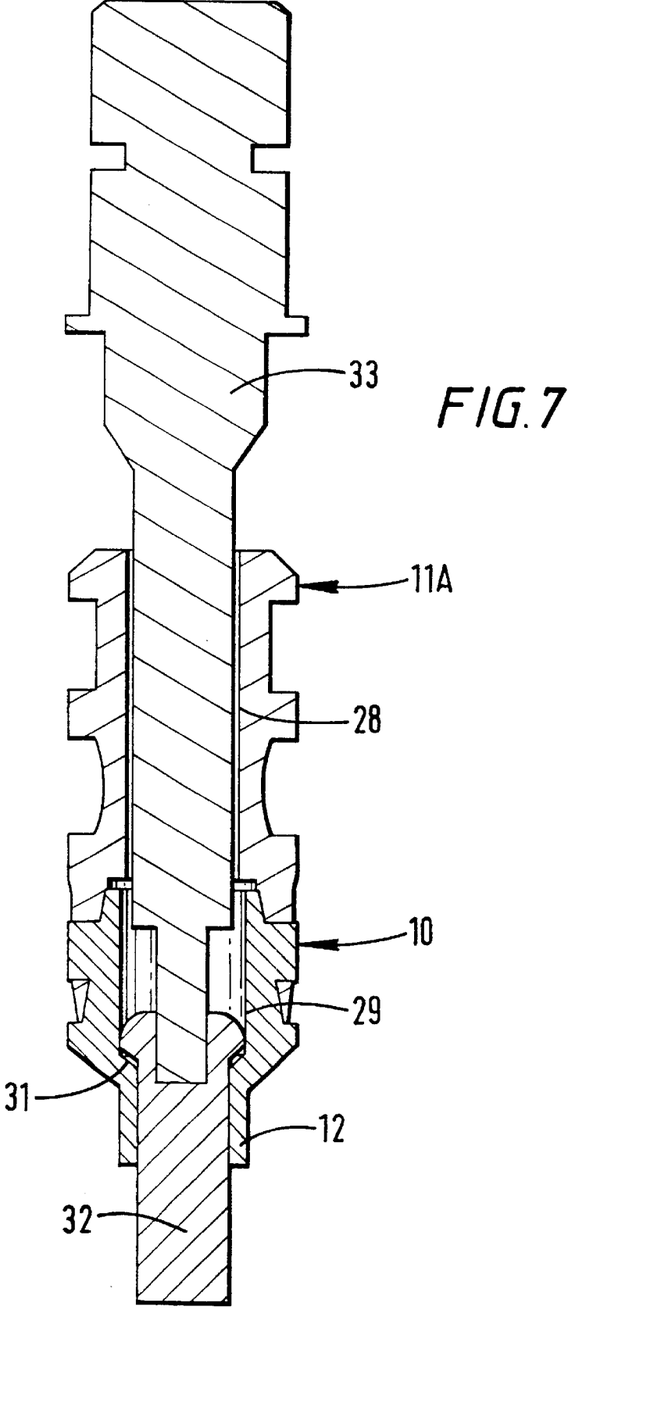
FIG. 7 is a section on the line VII—VII of FIG. 5.

FIG. 7 shows that the bore 29 of the post 10 is stepped, comprising one bore portion which extends through the hexagonal portion 12 and another, larger diameter bore portion which extends to the other end. An annular shoulder 31 separates the two portions of the bore 29. The fixing screw 32 has an enlarged head which seats on the shoulder 31. A hexagonal socket is formed in the head of the fixing screw 32. FIG. 7 also shows a screwdriver 33 inserted through the bore 28 of the coping 11A.

The diameter of the bore 28 is less than that of the larger diameter portion of the stepped bore 29 of the post 10. The screwdriver 33 has a hexagonal end which is fitted into the socket of the fixing screw 32 whereby the fixing screw 32 is turned by turning the screwdriver 33. It follows that the fixing screw 32 can be positioned within the post 10 and the respective coping 11 or 11A snap-fitted onto the post 10 by forcing the locating pins 17 into the respective keyhole slots 27 outside the mouth of the patient before the transfer jig is fitted into the implant. The fixing screw 32 will be entrapped within the coping 11 or 11A when the latter has been so assembled.

FIGS. 8 to 11 show another form of transfer jig which uses a different form of snap-fit connection between a generally tubular post 40 and a generally-tubular coping 41. Also the coping 41 is angularly located relative to the post 40 in a different way.

Figure 17:
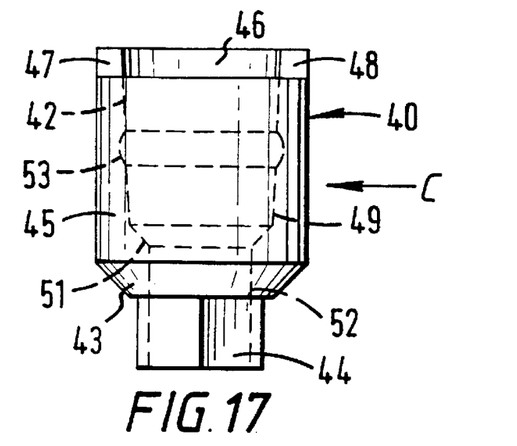
FIG. 17 is a side elevation of the post of the transfer jig shown in FIGS. 8 to 11.
Figure 18:
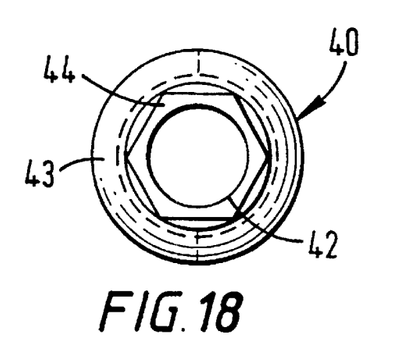
FIG. 18 is an underneath plan view of the post of FIG. 17.
Figure 19:
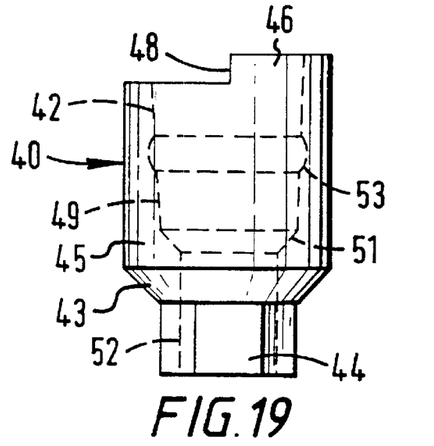
FIG. 19 is a view on arrow C of FIG. 17 of the post shown in FIG. 17.

Like the post 10, the post 40 has a stepped through bore 42 and a frusto-conical portion 43 which has a hexagonal portion 44 projecting coaxially from its smaller diameter end and a cylindrical portion 45 extending coaxially from its larger diameter end. The other end of the cylindrical portion 45 has a semi-circular arcuate wall portion 46 projecting axially beyond the semi-circular remainder. The diametrically opposed ends of the arcuate wall portion 46 form a co-planar pair of spaced radially-extending surfaces 47 and 48. The larger diameter bore portion 49 of the stepped bore 42 tapers towards the annular shoulder 51 that connects it to the smaller diameter bore portion 52. A circumferentially-continuous arcuate recess 53 is formed in the wall of the larger diameter bore portion 49 partway between the annular shoulder 51 and the arcuate wall portion 46.

Figure 10:
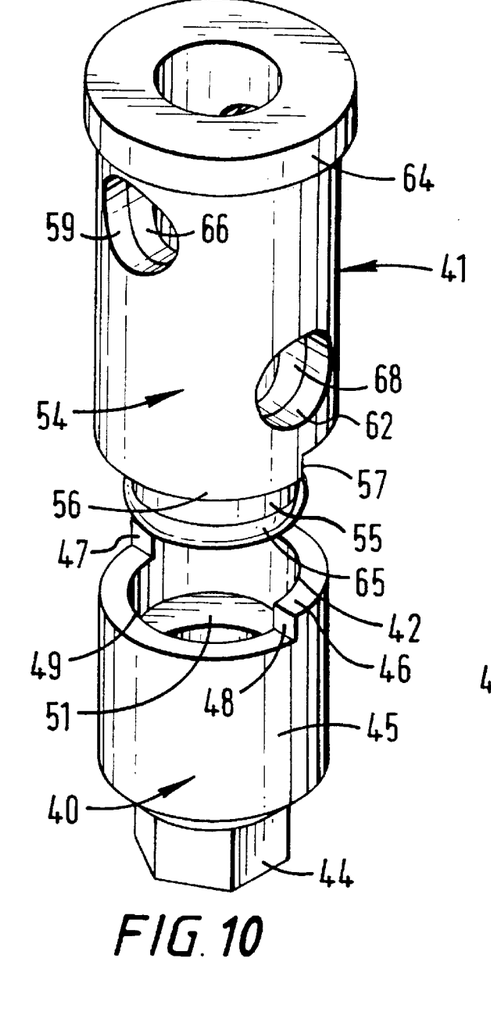
FIGS. 10 and 11 are views similar to FIGS. 8 and 9 respectively of the parts of the transfer jig of FIGS. 8 and 9 shown separated.
Figure 11:
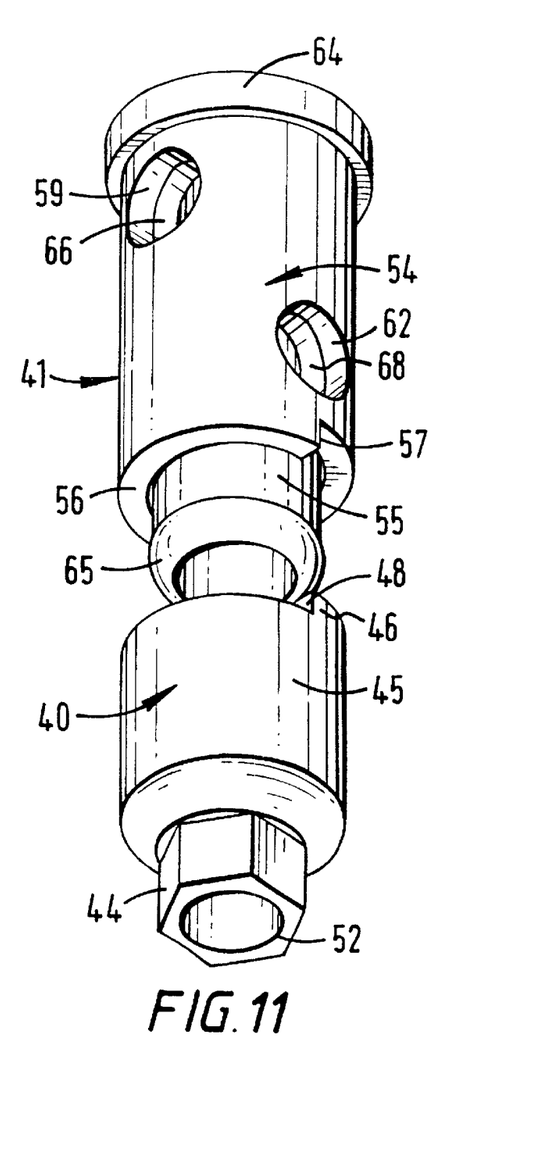

The coping 41 is formed in two parts for manufacturing convenience. One of its parts is a tubular sleeve 54 and the other is an inner tubular member 55.

Figure 14:
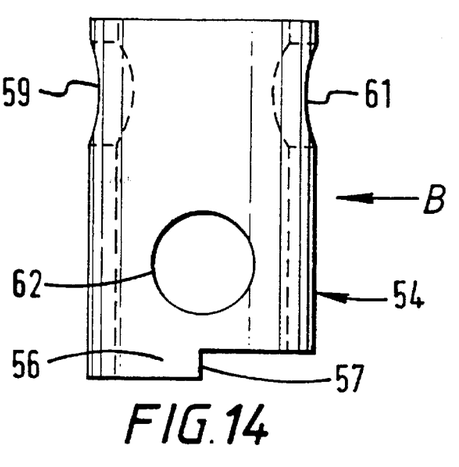
FIG. 14 is a side elevation of the outer tubular part of the coping of the transfer jig of FIGS. 8 to 11.
Figure 15:
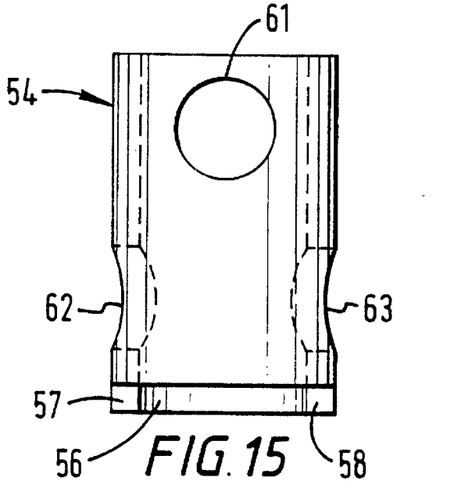
FIG. 15 is a view on arrow B of FIG. 14 of the part shown in FIG. 14.
Figure 16:
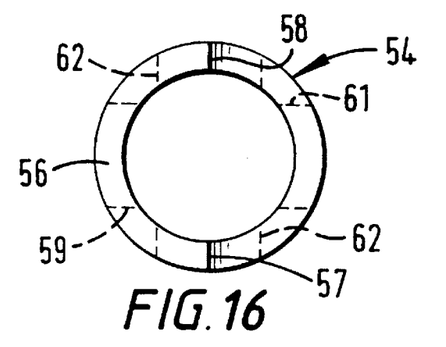
FIG. 16 is an underneath plan view of the part shown in FIG. 14.

The tubular sleeve 54 has a semi-circular arcuate wall portion 56 projecting axially beyond the semi-circular remainder at one end. The diametrically opposed ends of the arcuate wall portion 56 also form a co-planar pair of radially extending surfaces 57 and 58.

The height of the arcuate wall portion 56 beyond the semi-circular remainder of the respective end of the sleeve 54 is the same as that of the arcuate wall portion 46 of the post 40.

Two pairs of diametrically-opposed apertures 59 and 61, 62 and 63 are formed to extend through the tubular wall of the sleeve 54. Each pair of apertures 59 and 61, 62 and 63 is displaced angularly by about a right angle as well as axially from the other pair of apertures 59 and 61, 62 and 63.

Figure 12:
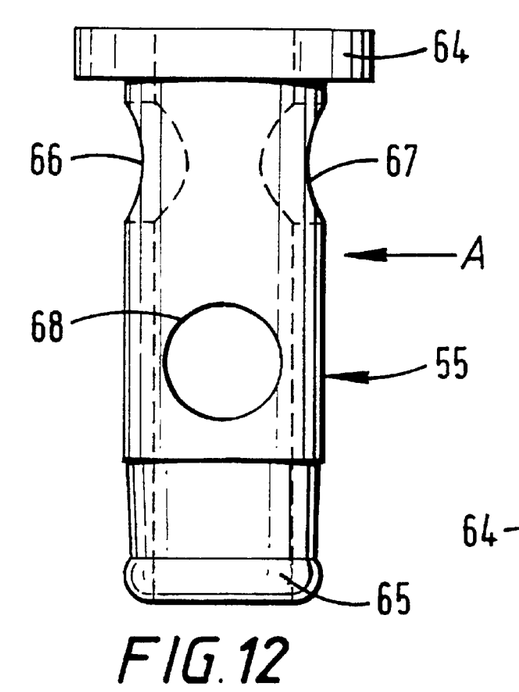
FIG. 12 is a side elevation of the inner tubular part of the coping of the transfer jig of FIGS. 8 to 11.
Figure 13:
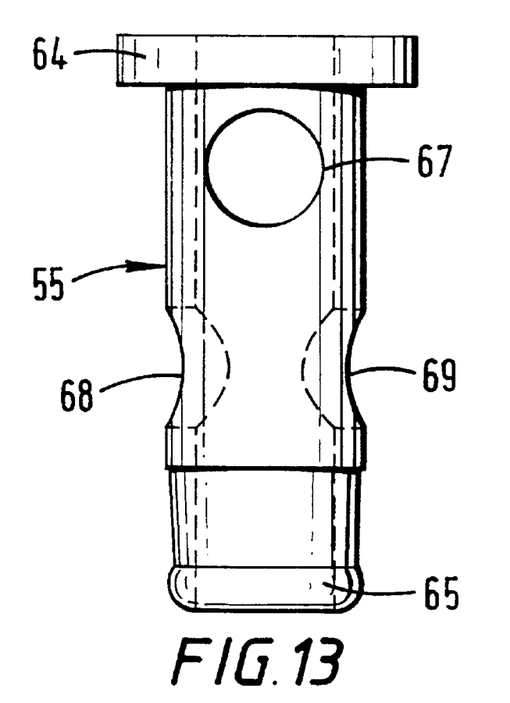
FIG. 13 is a view on arrow A of FIG. 12 of the part shown in FIG. 12.

The inner tubular member 55 has a radially-outwardly extending flange 64 at one end. It is longer than the tubular sleeve 54. It has an annular protuberance 65 formed at its other end, the surface of the protuberance 65 being a mirror image of the circumferentially-continuous arcuate recess 53 of the post 40.

Figure 8:
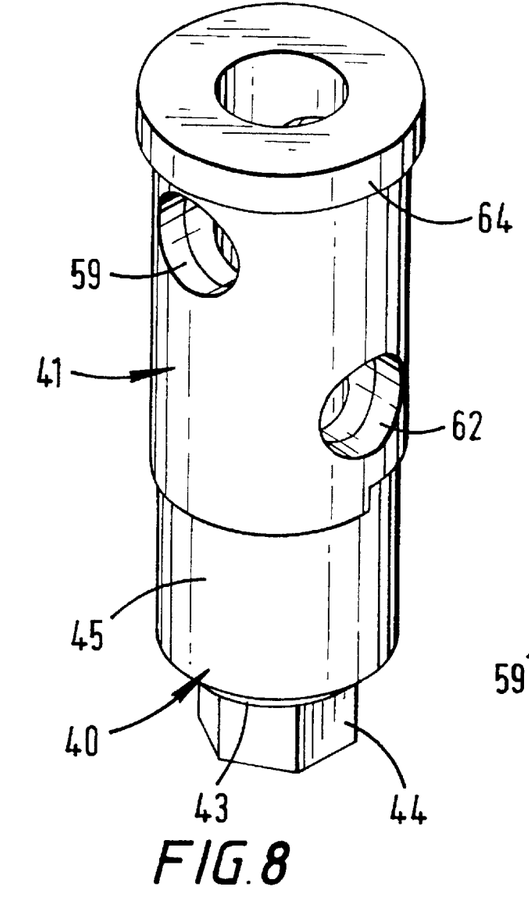
FIG. 8 is a perspective view of another alternative form of transfer jig.
Figure 9:
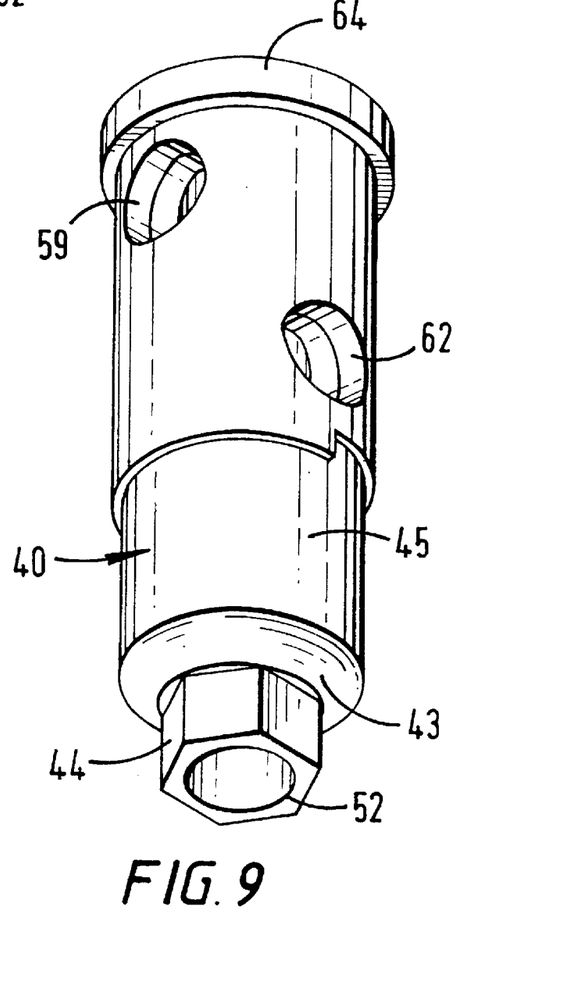
FIG. 9 is a perspective view of the transfer jig shown in FIG. 8 as seen from below in FIG. 8.

The sleeve 54 is fitted over the inner tubular member 55 so that its end remote from its arcuate wall portion 56 abuts the flange 64 of the tubular member 55 which is a tight fit in it. The tubular member 55 projects beyond the sleeve 54, as is shown in FIGS. 10 and 11, such that the annular protuberance 65 will be seated in the arcuate recess 53 and the two arcuate wall portions 46 and 56 will be seated on the semi-circular remainder of the other part 40,54 with their diametrically-opposed pair of radially extending surfaces 47 and 48, 57 and 58 in face to face abutment when the two parts 40 and 41 are snap-fitted together as shown in FIGS. 8 and 9 by pushing the projecting portion of the inner tubular member 55 into the larger diameter end of the tapered bore portion 49 of the tubular post 40.

FIGS. 12 and 13 show that the inner tubular member 55 has two pairs of apertures 66 and 67, 68 and 69 formed in it to extend through its tubular wall. The sizes, spacing and angular orientation of these apertures 66 to 69 in the inner tubular member 55 are substantially the same as for the apertures 59 and 61, 62 and 63 of the sleeve 54. The inner tubular member 55 and the sleeve 54 are fitted together so that each aperture in one of them is aligned with a respective aperture in the other such that the resultant coping 41 has through apertures communicating with its bore in the same way as does each of the copings 11 and 11A.

The procedure for using a transfer jig which includes a post 10 or 40 and a coping 11, 11A or 41 to form a dental prosthesis for mounting in an implant involves inserting the fixing screw 32 into the bore of the post 10,40 so that its threaded portion projects from the open end 52 of the bore 29,42 of the hexagonal portion 12,44, snap-fitting the coping 11,11A or 41 onto the post 10 ,40 so that, in the case of the copings 11 and 11A, its rim 23,23A is seated on the annular shoulder 16 of the post 10, fitting the hexagonal portion 12 into the standard hexagonal socket of the implant that is implanted in the jawbone of the patient and screwing the fixing screw 32 into the threaded hole in the implant, using the screwdriver 33 that is inserted through the bore 28 of the coping 11,11A or 41 and engaged in the hexagonal socket formed in the head of the fixing screw 32. It is more convenient to assemble the post 10,40, the fixing screw 32 and the coping 11,11A,41 outside the mouth of the patient before the hexagonal portion 12, 44 of the post 10,40 is fitted into the hexagonal socket of the implant and secured in place by the fixing screw 32 rather than to fit the post 10,40 into the hexagonal socket of the implant and to secure it in place before the coping 11,11A,41 is snap-fitted onto the post 10,40.

Either way, the locating pins 17 positively engage the sides of the slots 27 in the case of the post 10, or the radially extending surfaces 47 and 48, 57 and 58 are in face to face abutment in the case of the post 40, whereby the coping 11, 11A, 41 is spatially located with respect to the hexagonal portion 12, 44 which is fitted into the hexagonal socket of the implant.

A standard impression tray filled with an impression material, such as an elastomeric material, is inserted into the mouth of the patient, over the teeth, gums and transfer jig to create an impression. The impression material is forced through the apertures 24,24A, 59, 61–63, 66–69 in the cylindrical portion 19,19A, 54 and 55 of the coping 11,11A, 41, into the bores 28 and 29, 42 of the coping 11,11A,41 and around the flanges 21 amd 22, 21A and 22, 64. Such impression material may be injected into the bores 28 and 29, 42 through the open end of the coping 11,11A,41 remote from the post 10,40 since the screwdriver 33 would have been removed. When the impression material sets, the coping 11,11A,41 is locked in place in the set material, the flanges 21 and 22, 21A and 22A, 64 being embedded in the set material and the impression material within the bores 28 and 29, 42 of the coping 11,11A, 41 and the post 10, 40 being joined to the impression material that surrounds the transfer jig by the branches of impression material that extend through the apertures 24, 24A, 59,61–63, 65–69 and form structural links between the impression material within and surrounding the transfer jig.

Once the impression material has set, the impression tray is removed from the jaw, taking the impression material and the coping 11,11A,41 with it, the coping 11,11A,41 being separated from the post 10,40 to which it was snap-fitted. The post 10,40 may be removed from the implant by unscrewing the fixing screw 32 holding it in position, using the screwdriver 33. Alternatively, it may be left in place to serve as a healing collar while the dental prosthesis is being made.

The dental technician then uses the resulting impression as a maul to form a replica of the mouth of the patient and gums to enable the appropriate size of tooth or prosthesis to be made to the correct orientation.

The mounting arrangement embodying the present invention has a number of advantages, in particular, due to the particular configuration of the arrangement, it is not necessary for a special impression tray to be used. Also, if only a single tooth or several teeth need to be replaced, it may be possible to use the transfer jig shown in FIGS. 1 to 3 when the implant is first inserted, and an impression of the teeth and gums of a patient is taken at that stage. This eliminates the need for exposing the implant at a later stage, for example some three to six months after insertion of the implant, to take the impression prior to inserting the final tooth.

Various modifications will be appreciated by the persom skilled in the art, for example, whilst the post 10, 40 has been described as being formed from a metal, such as titanium, it could be formed from a plastics material. Similarly the coping has been described as being formed from a plastics material, however, other materials could be used. Also, the number and position of the apertures in the coping through which the impression material is forced, may vary from that illustrated and described above, as may the number, form and location of the locating pins and receiving slots or other means for locating the coping with respect to the hexagonal portion of the post.

Furthermore, the transfer jigs described above need not be connected directly to an implant having an internal hexagonal socket, but may be fitted to the implant via an angled core (not shown). As a range of differently angled cores are generally available, it is possible to select the appropriately angled core for the particular patient into which the transfer jigs described above may be inserted.

In a further preferred embodiment, the post 10 may have one or the other or both of the frusto-conial portions and/or the interconnecting cylindrical portion offset at an angle to the central longitudinal axis of the hexagonal portion. The angle at which these portions may be offset could be, for example, in the range 0 to 45 degrees. Also, it may be possible to construct the aforementioned portions such that a variety of posts are produced having differing angular orientations around the axis of the hexagonal portion. The advantage of these arrangements is that a maul in which the precise angular orientation for the ultimate dental prothesis is formed may be obtained.

The geometrical relationship between the hexagonal portion 12,44 and the locating pins 17 or the radially-extending surfaces 47 and 48 needs to be the same for all posts 10, 40 so as to ensure interchangeability and accurate reproduction of the orientation of the coping 11,11A,41 with respect to the implant in the resultant prosthesis.

What is claimed is:

1. A dental formation mounting arrangement including:
    a locating element having a portion formed to be a snug fit in a socket formed in a dental foundation member on which a dental formation is to be mounted,
    a fixing structure fixing the locating element to the foundation member when the locating element portion is fitted into the socket, and
    a mating element attachable to and detachable from the locating element by a snap-fit attachment,
    said locating element having a flat surface which is adapted to make face to face contact with a corresponding flat surface of the socket when that locating element portion is fitted into the socket whereby to hold the locating element against rotation relative to the dental foundation member;
    each of the locating and mating elements being provided with a respective formation, the formation on the locating and mating elements being positively interengageable when the mating element is snap-fitted onto the locating element and the mating element is in a certain orientation relative to said flat surface,
    wherein the mating element is a hollow body provided with apertures in its structure which place its interior in communication with its surrounds,
    the arrangement being such that, when the mating element is embedded in dental impression material during a process of making a dental impression, such dental impression material can extend through the apertures and form structural links between such dental impression material within the interior of the hollow body and such dental impression material that surrounds the hollow body.

2. A dental formation mounting arrangement according to claim 1, wherein the snap-fit comprises:

at least one locating member which protrudes from one of the locating and mating elements, the at least one locating member being locatable in a corresponding recess formed in the other of the locating and mating elements, said at least one locating member and said corresponding recess serving as said formations.

3. A dental formation mounting arrangement according to claim 2, wherein said at least one locating member protrudes from the locating element and is locatable in a respective slot in the mating element.

4. A dental formation mounting arrangement as in claim 1, wherein the locating element is formed from metal.

5. A dental formation mounting arrangement as in claim 1, wherein the mating element is formed from a plastics material.

6. A dental formation mounting arrangement as in claim 1, wherein the mating element includes at least one flange which is embeddable in a dental impression material in use, enabling the mating element to be removed with the impression material once the impression material has set.

7. A dental formation mounting arrangement as in claim 1, wherein:

said locating and mating elements are structured to snap-fit together by pushing a projecting portion of one of them into a cavity formed in the other and said formations include a wall which extends partway around the mouth of the cavity and which seats substantially without clearance in a corresponding recess formed in said one of said locating and mating elements, movement of said other element relative to said one element in the direction that would displace the wall around the periphery of the cavity being stopped by abutment with the ends of the recess in which the wall seats without substantial clearance.

8. A dental formation mounting arrangement including:

a locating element having a portion formed to be a snug fit in a socket formed in a dental foundation member on which a dental formation is to be mounted, a fixing structure fixing the locating element to the foundation member when the locating element portion is fitted into the socket, and a mating element attachable to and detachable from the locating element by a snap-fit attachment, said locating element having a flat surface which is adapted to make face to face contact with a corresponding flat surface of the socket when that locating element portion is fitted into the socket whereby to hold the locating element against rotation relative to the dental foundation member;

each of the locating and mating elements being provided with a respective formation, the formation on the locating and mating elements being positively interengageable when the mating element is snap-fitted onto the locating element and the mating element is in a certain orientation relative to said flat surface, wherein the snap-fit structure comprises at least one locating member which protrudes from one of the locating and mating elements, the at least one locating member being locatable in a corresponding recess formed in the other of the locating and mating elements, said at least one locating member and said corresponding recess serving as said formation; and wherein said at least one locating member comprises one or more locating pins.

9. A dental formation mounting arrangement as in claim 8 wherein said at least one locating member protrudes from the locating element and is locatable in a respective slot in the mating element.

10. A dental formation mounting arrangement including:

a locating element having a portion formed to be a snug fit in a socket formed in a dental foundation member on which a dental formation is to be mounted, a fixing structure fixing the locating element to the foundation member when the locating element portion is fitted into the socket, and a mating element attachable to and detachable from the locating element by a snap-fit attachment, said locating element having a flat surface which is adapted to make face to face contact with a corresponding flat surface of the socket when that locating element portion is fitted into the socket whereby to hold the locating element against rotation relative to the dental foundation member;

each of the locating and mating elements being provided with a respective formation, the formation on the locating and mating elements being positively interengageable when the mating element is snap-fitted onto the locating element and the mating element is in a certain orientation relative to said flat surface, wherein said locating and mating elements are structured to snap-fit together by pushing a projecting portion of one of them into a cavity formed in the other and said formations include a wall which extends partway around the mouth of the cavity and which seats substantially without clearance in a corresponding recess formed in said one of said locating and mating elements, movement of said other element relative to said one element in the direction that would displace the wall around the periphery of the cavity being stopped by abutment with the ends of the recess in which the wall seats without substantial clearance.

11. A method for making a model of at least part of the gum and one or more adjacent teeth that surround one or more dental foundation members embedded in the jawbone of a patient, said one or more dental foundation members each having a receiving socket therein, the method including:

(i) locating a locating element in the socket of the or each dental foundation member;

(ii) attaching a mating element to the locating element by means of a snap-fit;

(iii) placing a dental impression tray filled with dental impression material around the teeth, gums and the or each dental foundation member;

(iv) removing the impression tray and dental impression material with the mating element embedded therein from the mouth of the patient by overcoming the snap-fit holding the mating element on the locating element once the dental impression material has set; and (vii) forming a replica of the teeth and gums of the patient using the impression created in the dental impression material once set, as a maul;

(viii) providing the socket and a portion of the locating element which is located in the socket with mating flat faces which make face to face contact with one another when the locating element is located in the socket whereby the locating element is held against rotation relative to the dental foundation member;

(ix) positively interengaging certain formations provided on the locating and mating elements so that the mating element is in a certain orientation relative to said dental formation member, and (x) selecting a hollow body as the mating element, the hollow body having apertures in its structure which place its interior in communication with its surrounds and, filling the interior with dental impression material so that it extends through the apertures and forms structural links between the dental impression material within the hollow body and the dental impression material that surrounds the body in the tray.

12. A dental formation mounting device, said device comprising:

a first unit fixable to a dental foundation on which a dental formation is to be mounted and having a locating region and at least one mating formation, said locating region being insertable in a socket provided in said dental formation and adapted such that when so inserted relative rotation between the first unit and dental foundation is prevented; and a second unit attachable to said first unit in a predetermined orientation relative thereto, said second unit having at least one second mating formation releaseably snap-fittable with a respective said first mating formation such that said second unit can be releaseably held in said predetermined orientation relative to said first unit;

said first and second mating formations including a projection and a recess for receiving the projection; and wherein said recess comprises an elongate slot defined by said second unit and extending in a lengthways direction of said second unit.

13. A dental formation mounting device, said device comprising:

a first unit fixable to a dental foundation on which a dental formation is to be mounted and having a locating region and at least one mating formation, said locating region being insertable in a socket provided in said dental formation and adapted such that when so inserted relative rotation between the first unit and dental foundation is prevented; and a second unit attachable to said first unit in a predetermined orientation relative thereto, said second unit having at least one second mating formation releaseably snap-fittable with a respective said first mating formation such that said second unit can be releaseably held in said predetermined orientation relative to said first unit;

wherein said second unit comprises a sleeve and a cylindrical member insertable into said sleeve, wherein said cylindrical member and said sleeve each have recesses defined therein, the arrangement being such that on insertion of said cylindrical member into said sleeve, the recesses can be aligned to define at least one transverse through-hole in said second unit.

14. A device as in claim 13 wherein said first unit comprises a bore for a screw by which said first unit can be releaseably fixed to said dental foundation member.

15. A device as in 13 wherein said first unit and second unit are provided with respective abutment surfaces which define said predetermined orientation.

16. A device as in claim 13 wherein said first and second mating formations are adapted to define said predetermined orientation.

17. A device as in claim 13 wherein said first and second mating formations comprise a projection and a recess for receiving the projection.

18. A device as in claim 13 wherein said locating region has a hexagonal peripheral surface.

19. A device as in claim 13 wherein said second unit is attachable to said first unit by axial push-fitting.

20. A device as in claim 13, wherein said recess comprises an elongate slot defined by said second unit and extending in a lengthways direction of said second unit.

21. A dental formation mounting arrangement comprising:

a post member affixable in a pre-determined position to a receiving socket of an implanted dental foundation member; and an apertured coping member releasably affixable in a pre-determined rotational position to said post member;

said apertured coping member including plural apertures therethrough such that, in use, dental impression material may flow into and through said apertures to create, when cured, structural links of cured dental impression material extending through apertures between cured bodies of dental impression material residing inside and outside said coping member.

22. A method for making a model of mouth structures surrounding a dental formation mounting arrangement, said method comprising;

affixing a post member in a pre-determined position to a receiving socket of an implanted dental foundation member;

releasably affixing an apertured coping member in a pre-determined rotational position to said post member, said apertured coping member including plural apertures therethrough; and causing dental impression material to flow into and through said apertures and around surrounding mouth structures to create, when cured, structural links of cured dental impression material extending through apertures between cured bodies of dental impression material residing inside and outside said coping member.

* * * * *